US005790247A

United States Patent [19]

Henley et al.

[11] Patent Number: 5,790,247
[45] Date of Patent: Aug. 4, 1998

[54] TECHNIQUE FOR DETERMINING DEFECT POSITIONS IN THREE DIMENSIONS IN A TRANSPARENT STRUCTURE

[75] Inventors: Francois J. Henley, Los Gatos; Michael A. Bryan, Oakland, both of Calif.

[73] Assignee: Photon Dynamics, Inc., San Jose, Calif.

[21] Appl. No.: 721,332

[22] Filed: Sep. 26, 1996

[51] Int. Cl.⁶ ................................................ G01N 21/17
[52] U.S. Cl. ............................................ 356/237; 356/239
[58] Field of Search .................................. 356/237, 239, 356/338, 394; 250/559.42; 348/125, 127, 128

[56] References Cited

U.S. PATENT DOCUMENTS

| | | | |
|---|---|---|---|
| 4,808,813 | 2/1989 | Champetier | 356/239 |
| 5,177,559 | 1/1993 | Batchelder et al. | 356/237 |
| 5,268,735 | 12/1993 | Hayshi | 356/239 |
| 5,355,213 | 10/1994 | Dotan | 356/239 |
| 5,515,159 | 5/1996 | Sites et al. | 356/239 |
| 5,631,733 | 5/1997 | Henley | 356/237 |

FOREIGN PATENT DOCUMENTS 0044587  4/1979  Japan ................. 356/239

*Primary Examiner*—Hoa Q. Pham
*Attorney, Agent, or Firm*—Townsend and Townsend and Crew LLP; Kenneth R. Allen

[57] ABSTRACT

A method (500) for inspecting anomalies, which are likely defects of several types, namely, particles on the surface, scratches into surface, and defects in bulk material, is provided. This inspection method involves two types of illumination, which can be used separately or together. These two types highlight anomalies sufficiently differently to enable the defect monitoring tool to distinguish between defect type and defect location along an inspection axis. The illumination methods are direct internal side illumination (114) where the plate is used as light pipe, and external front-side illumination (117). In direct internal side illumination, a fiber optic feed (115) with flared end arranged as a line source is abutted to an edge (123) of the plate (102). In external side illumination, the source is light directed at an acute angle, preferably a grazing angle, to one of the surfaces (121). Anomalies such as dust particles on the illuminated surface will scatter light much more efficiently with external front-side illumination, than direct internal side lighting, since particles on the surface would otherwise scatter light only through weak evanescent coupling via the internal side lighting.

23 Claims, 6 Drawing Sheets

TECHNIQUE FOR DETERMINING DEFECT POSITIONS IN THREE DIMENSIONS IN A TRANSPARENT STRUCTURE

This present invention relates to defect monitoring tools and related methods for inspection of structures useful in, for example, large flat panel display construction. More particularly, the invention is illustrated in an example related to the inspection of glass plates for use in flat panel displays. But it will be recognized that the invention also can be applied to the manufacture of almost any type of transparent media.

The use of a flat panel display such as a liquid crystal display (LCD) or the like continues to grow rapidly. For example, consumer items such as a pocket TV, a notebook computer, an engineering work-station, a high-definition television (HDTV), and others use such a display. Based upon the continued demand for this display, industry has made massive capital investments in creating state-of-art manufacturing lines.

These state-of-art manufacturing lines, however, still rely upon human test operators for the final test and inspection of these flat panel displays. The test operator performs a visual inspection of each display for defects in order to accept or reject the display. The quality and completeness of the inspection is dependent on the test operator, who has been trained using limited samples of displays that have defects and characterized as either pass or fail. The inspection results are highly subjective and prone to error, and cannot be used effectively and efficiently to monitor, control, and improve the quality of the various manufacturing processes.

Effective process monitoring and control of flat panel display production have been made possible through quantitative inspection methods by way of automatic inspection machines. An example of one of the first pioneering automatic inspection machines was developed by Photon Dynamics, Inc. (PDI) in 1992, assignee of the present application. This first automatic inspection machine is pioneering, since a high quality inspection of flat panel displays could be performed using machines, rather than human test operators. This high quality inspection was performed on flat panel displays having completed thin film transistor components fabricated thereon.

Industry now desires an effective technique for identifying defects in glass plates used for the manufacture of these flat panel displays. Glass plates generally have a front-side surface and a back-side surface. The front-side surface must be substantially defect or anomaly free, since thin film transistors will be fabricated thereon. Defects, however, may exist to a greater degree on the back-side surface and within the bulk medium of the plate. Accordingly, glass plates having only bulk medium and/or back-side surface defects must be separated from those plates having any defects located on the front-side surface.

A human test operator often inspects the glass plates for the presence of these defects during their inspection. The test operator performs a visual inspection of each glass plate for defects in order to accept or reject the plate depending upon its defects. The quality and completeness of the inspection is dependent on the test operator, who has been trained using limited samples of plates that have defects and characterized as either pass or fail. The inspection results are highly subjective and prone to error, and cannot be used effectively and efficiently to monitor, control, and improve the quality of the various manufacturing processes used for the glass plates.

From the above, it can be seen that a technique for identifying defects on a glass plate that is easy, cost effective, and reliable is often desirable.

SUMMARY OF THE INVENTION

According to the present invention, a technique including a method and apparatus for identifying anomalies in a transparent medium is provided. This technique uses a large area defect monitoring tool having two types of illumination, namely, external and internal lighting, to highlight anomalies and their relative location in the transparent medium, e.g., glass substrates, etc.

In one aspect of the invention, a method for inspecting anomalies, which are likely defects of several types, namely, particles on the surface, scratches into surface, and defects in bulk material, is provided. This inspection method involves two types of illumination, which highlight anomalies sufficiently differently to enable the defect monitoring tool to distinguish between defect type and defect location along an inspection axis. The illumination methods are direct internal side illumination where the plate is used as a "light pipe," and external front-side illumination. In direct internal side illumination, a fiber optic feed with flared end arranged as a line source is abutted to an edge of the plate. In external side illumination, the source is light directed at an acute angle, preferably a grazing angle, to one of the surfaces. Anomalies such as dust particles on the illuminated surface will scatter light much more efficiently with external front-side illumination, than direct internal side lighting, since particles on the surface would otherwise scatter light only through weak evanescent coupling via the internal side lighting.

In another aspect of the invention, the location of the anomalies along the inspection axis can be determined by as little as two measurements where the location of focus is alternately above and below the plane of the plate, which is the inspection target. A difference in signal levels from these locations illuminated differently, or illuminated at different distances, along the inspection axis are used to determine type and location of anomalies along the inspection axis.

The present invention also provides an apparatus for locating defects on a first surface, on a second surface, and in a transparent planar medium with an optical image area defect monitoring tool. The apparatus has a light source for illuminating the planar medium at an angle to an inspection axis, in order to highlight external and internal optical anomalies. The inspection axis is substantially normal to the planar medium. A (charge-coupled device) CCD camera is operably coupled to an image processor. This CCD camera and image processor capture first images of the anomalies in a first vertical position away from a center of the planar medium at a first out-of-focus location on a first side of the planar medium, and identify the first images as first events in two-dimensional locations, e.g., x-y, r-θ, etc. The CCD camera and image processor also capture second images of the same anomalies in a second vertical position away from a center of the planar medium at a second out-of-focus location on a second side of the planar medium opposite to the first side, and identify the second images as second events in the two-dimensional locations. The image processor further processes the first and second images to generate a corresponding first signal level and a second signal level. Differences between the first signal level and the second signal level are indicative of a z-location of the anomalies along the inspection axis.

A further aspect of this invention provides an apparatus for providing internal and external illumination to a glass plate. This plate comprises a possible anomaly, such as a gouge, a crack, a particle, a void, or the like. The plate is a transparent medium with a front-side surface, a back-side surface, and a medium located therebetween. This medium has a refractive index greater than one. The plate also has an edge defined along a boundary of the front-side surface, the medium, and the back-side surface. An optical coupling (e.g., fiber optic flare, etc.) is attached to the edge. The optical coupling provides light to the edge. This light enters the medium through the edge and traverses through the medium. A portion of the light internally reflects off the front-side surface and the back-side surface, but another portion of the light can scatter off of a possible anomaly in the medium. This scattered light is emitted through the front-side surface, and is to be detected by a CCD camera. The apparatus also has an external illumination means for projecting a second light onto the front-side surface. This second light is adapted to scatter off of a possible anomaly, which is located at the front-side surface.

The invention will be better understood by reference to the following detailed description in connection with the accompanying drawings.

DESCRIPTION OF SPECIFIC EMBODIMENTS

Figure 1:
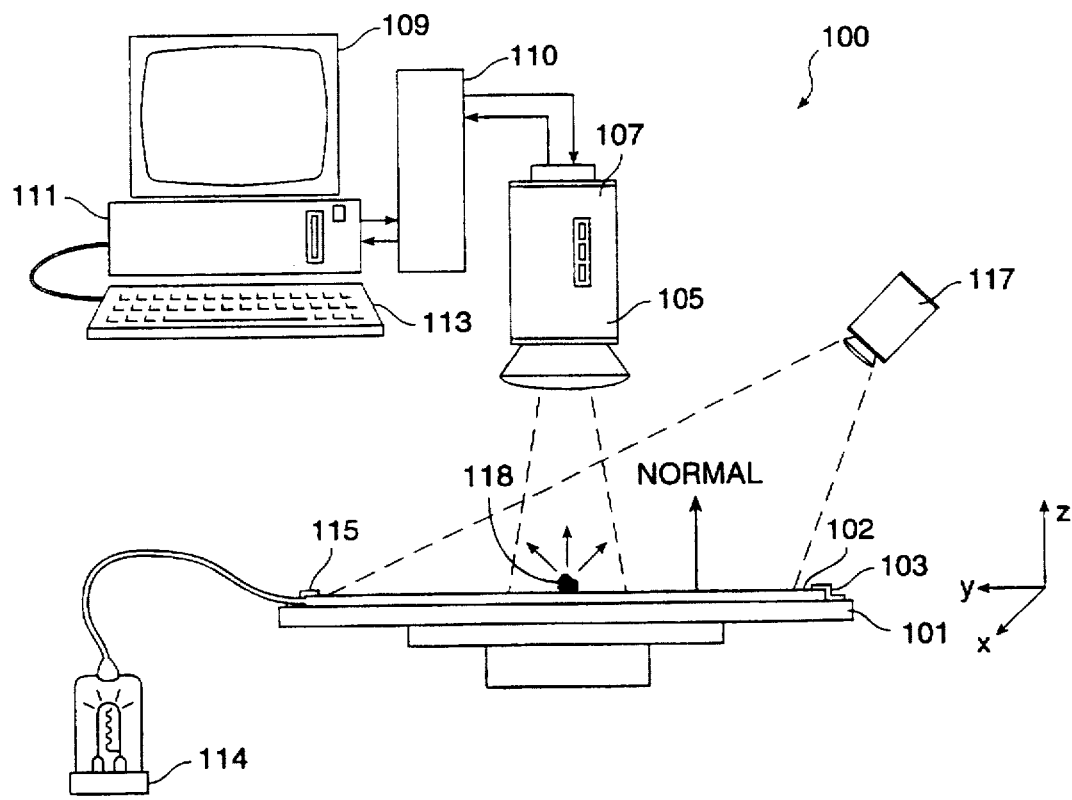
FIG. 1 is a simplified diagram of an apparatus according to the present invention.

Referring to FIG. 1, the present invention includes an inspection apparatus 100, e.g. large area defect monitoring tool. The inspection apparatus 100 is merely an illustration and should not limit the scope of the claims as defined herein. The inspection apparatus 100 includes a transparent plate 102 such as a glass plate and the like. This plate positions on a slidable table 101, and a hinged frame 103, which is brought down to secure the plate in place. The slidable table 101 allows for easy positioning of the plate in an x-y plane under a plurality of cameras 105, such as multiple CCD-type cameras and the like. The slidable table allows for the plate to be shifted in the x-y directions relative to the cameras. Alternatively, the cameras are mounted onto an x-y stage to move the cameras relative to the plate. Alternatively, multiple cameras can be used to increase viewing angle.

The x-y stage can be any suitable base unit capable of moving the plate in an x-direction and/or a y-direction. The stage may include continuous movement in the x-direction and/or y-direction. Preferably, the x-y stage also increments at selected dimensions in the x-direction and the y-direction. Alternatively, a robot can move the plate in the x-y directions.

The z-direction operates in a continuous movement mode or at selected z-positions through the use of an actuator. The actuator can be in a two-stage or multi-stage actuator. The z-direction may also operate in a stepping mode. Of course, exact incremental dimensions in the x-direction, the y-direction, and the z-direction depend upon the particular application. In other embodiments, the stage has movement in the z-direction, but does not adjust in the x-y direction during inspection. In further embodiments, the cameras are adjustable in the z-direction relative to the plate.

Figure 2:
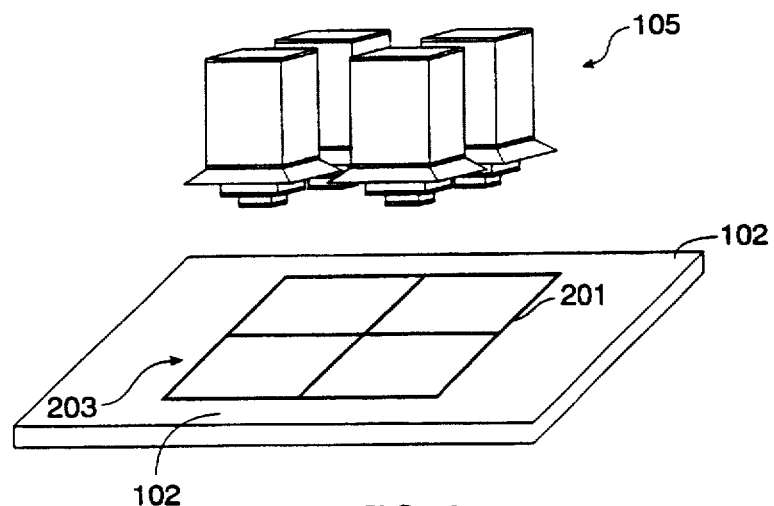
FIG. 2 is a simplified diagram of an array of CCD cameras for the FIG. 1 apparatus.

The CCD cameras can be selected from conventional high resolution CCD-type cameras. An example of such a CCD camera can use a megapixel CCD array such as the KAF1600, made by Kodak. In one embodiment, the CCD cameras are grouped or catenated into an array structure of similar CCD cameras. This grouping of CCD cameras allows for inspection of larger surface areas using less snap-shots of the front-side surface of the plate. The similar CCD cameras can be grouped with other similar CCD cameras to form an array structure of similar CCD cameras (e.g., four-cameras, etc.), as illustrated by FIG. 2. In a preferred embodiment, each CCD camera uses a 1K pixel by 1K pixel array to capture a 100 mm by 100 mm plate surface region 201. These four CCD cameras can capture a total surface glass surface region 203 of 200 mm by 200 mm. The four similar CCD cameras can be grouped together in a grouping of four to form an array structure of sixteen similar CCD cameras. The sixteen CCD cameras then can be grouped into another array structure to form sixty-four similar CCD cameras. Preferably, these cameras 105 are encased with an upper body 107 of the inspection apparatus. A monitor 109, an image processor 110, a computer 111, and a keyboard 113 are also shown.

Image processor 110 can be selected from a variety of conventional high performance processors. An example of such a processor is a MV200 made by DATACUBE. This processor includes features such as large memory capacity and flexible array processing, among others. Preferably, the image processor has multiple input/output ports for multiple CCD cameras and the like. Of course, the type of processor used depends upon the application.

Figure 3:
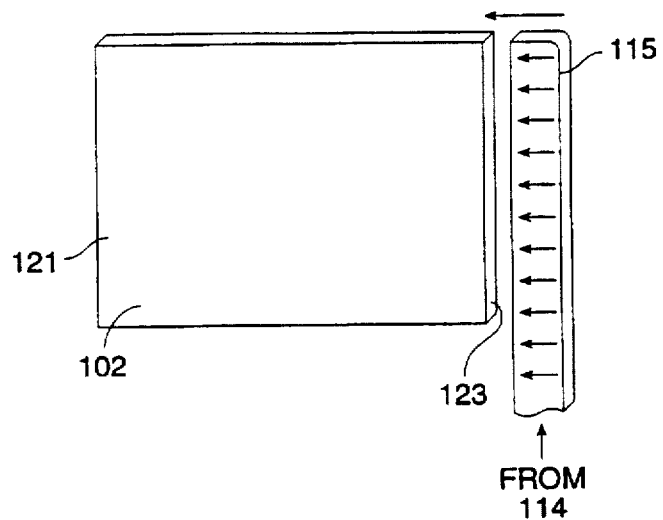
FIG. 3 is a simplified side-view diagram for the optical coupling of FIG. 1.

The present apparatus includes a light source 114 providing internal edge illumination to the plate 102. An optical coupling 115 (or connector), which is coupled to or attached to an edge of the plate, supplies light from the light source 114 to an edge of the plate 102. FIG. 3 is a simplified side-view diagram of the plate 102 and the optical coupling 115 of FIG. 1. This side-view diagram is merely an illustration, and should not limit the scope of the claims as defined herein. The light source 114 emits a beam of light into the connector 115. The light can be diffused, collimated, or the like. An example of such a light source is quartz tungsten-halogen (QTH) or xenon, but also can be others. This light source provides a light having a wavelength range in the visible to IR (450–900 nm), compatible with silicon CCD sensitivities. Preferably, the wavelength is about 600 or less. Of course, the type of light source will depend upon the application.

The plate 102 includes a front-side surface 121, an outer edge 123, and other elements. The plate can be transparent glass such as a glass plate or the like. This transparent plate often has a substantially planar front-side surface 121, but also can have other shapes. An example of such a glass plate is made by Corning, Inc. of New York sold under the product name of Corning 7059 glass. This glass is often used in the manufacture of flat panel displays and the like. The glass plate has a refractive index of about 1.5 and a 1.1 mm to 0.7 mm thickness. Of course, the plate can almost be any relatively transparent structure or medium with a refractive index greater than one, relative to its surroundings.

Figure 4:
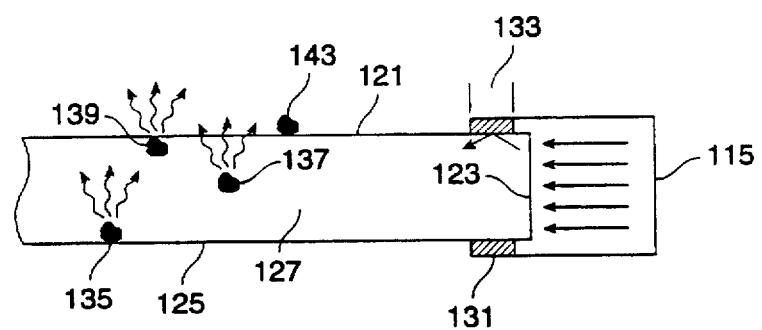
FIG. 4 is a simplified cross-sectional view diagram for the optical coupling of FIG. 3.

FIG. 4 is a more detailed cross-sectional view diagram of the plate 102 and optical coupling of FIG. 3. This cross-sectional view diagram is merely an illustration, and should not limit the scope of the claims as defined herein. This simplified cross-sectional view diagram includes the plate 102 and the optical coupling 115. An example of this coupling is an optical flare, such as those used in fiber optic applications. By firmly engaging this coupling to one 123 of the plate ends, light from this source enters internally into the plate through the edge 123 of the plate, without substantial reflection. In one embodiment, light from the coupling enters through the edge 123 of the plate, and travels along the bulk medium 127 between its front-side surface 121 and its back-side surface 125. The front-side surface 121 and back-side surface 127 act as a "light pipe" for the light entering the plate edge. As the light pipe, a substantial portion of the light reflects off the inner-sides of the front and backside surfaces, and traverses along the bulk medium. In one embodiment, substantially all of the light reflects internally off of the inner-sides after the first reflection. Preferably, the first reflection occurs in an exclusion region 133. In particular, a portion of the light reflects off coupling wall 131, which extends over the exclusion region 133 of the plate.

The coupling wall can be made of a light absorbing material on a stable reference (or ball) material made of stainless steel, coated steel or aluminum, selected alloys, and the like. These materials have sufficient structural strength to firmly attached to the plate, and the light absorbing quality can absorb light derived from the optical coupling out of the bulk glass medium. The reflected light from total internal reflection traverses along the medium in the x-y directions. It will be observed that the reflected light will internally reflect off the front-side and back-side surfaces as it traverses along the x-y directions.

Any anomaly or event in the plate medium which prevents total internal reflection, however, causes the light to scatter through the front-side surface or the back-side surface. This scattering is shown by the arrows from the anomalies 135, 137, and 139 on the inner back-side surface 125, the bulk medium 127, and the inner front-side surface 121, respectively. Preferably, a substantial portion of the light scatters through the front-side surface for detection at one of the CCD cameras. This CCD camera will detect the presence of the event or the anomaly by reading an increased light intensity value against normal background intensity. An anomaly 143 on the plate surface 121, however, will not substantially scatter from the internally reflected light. Accordingly, anomalies in the bulk glass medium can be selectively detected over the anomalies on the front-side surface. Preferably, anomalies having a dimension less than about 0.1–1 µm are detected by one of the CCD cameras using this edge illumination technique.

In one embodiment, the present apparatus also includes an external light source 117 for illuminating the front-side surface of the plate, as illustrated by FIG. 1. This external light source provides a collimated beam of light incident upon the front-side surface. In one embodiment, the collimated beam of light can be incident upon the front-side surface at an angle ranging from about 70° to about 85° from the normal to the front-side surface. Preferably, the collimated beam of light is incident upon the front-side surface at an angle 90° from the normal to the front-side surface. This embodiment produces a shallow angle where the illuminator becomes a dark field illuminator, where no specularly reflected light is captured by the CCD cameras. In almost all embodiments, the angle is an acute angle from the normal to the front-side surface, and the angle is, at times, a grazing angle sufficient to cause scattering off of an anomaly 118 on the front-side surface. In this example, the anomaly is a particle. Of course, the particular angle will depend upon the application.

The light source can be any suitable lighting means such as quartz tungsten halogen, xenon or mercury-arc lamps to provide illumination to the front-side surface. A mercury light source, for example, can provide light having a wavelength of about 253.7 nm. Optionally, the light source can have a lens adapted thereto. This lens can be used to focus the light source and its illumination on the front-side surface of the plate. In other embodiments, the light source can include multiple light sources. These multiple light sources are disposed at different angles incident to the front-side surface of the plate, and can be adjusted to increase the amount of scattering from any anomalies on the front-side surface. Filters also can be used with the light source to increase the amount of scattering off the anomalies. Of course, the particular light source(s) depends upon the application.

This external illumination is selectively projected onto the surface of the front-side to cause light to scatter from anomalies. Specifically, projected light incident to the front-side surface reflects off of this front-side surface based upon its incident angle. Anomalies on the front-side surface, however, will scatter the projected light. Scattered light as depicted by the arrows in FIG. 1 will traverse through the surroundings, typically air. One CCD camera will detect the scattered light as an increased light intensity against normal background intensity. The increased light intensity signifies the presence of an anomaly, e.g., particle, chip, scratch, gouge, void, etc.

In one embodiment, front-side illumination can be used by itself to illuminate anomalies on the front-side surface only due to evanescent coupling, and more particularly to an electric field distortion near the defect. By using only front-side illumination, anomalies on the front-side surface will be selectively detected over anomalies in the bulk glass media or back-side surface. An anomaly having its smallest dimension of about 0.1–1 µm and less can be detected by way of this present invention. Identifying the presence of these anomalies on the front-side surface is important in the inspection of, for example, glass plates used for flat panel displays.

In alternative embodiments, external light illumination and internal edge illumination are used together. These embodiments highlight the anomalies through the entire plate, e.g., back-side surface, front-side surface, and bulk media. Highlighted anomalies are detected with CCD cameras. Of course, other types of illumination also may be used depending upon the application.

A method according to the present invention is provided to identify anomalies or defects using the present lighting techniques. The present method may be briefly outlined as follows.

(1) Provide plate onto a plate holder.
(2) Illuminate plate using either front-side illumination or edge illumination or both illumination techniques.

(3) Measure plate using CCD cameras and capture images of anomalies.

(4) Threshold images of anomalies to find events.

(5) Store events using a coordinate system (e.g., x-y, r-θ, etc.)

(6) Define a centroid for each of the events.

(7) Categorize events.

Figure 5:
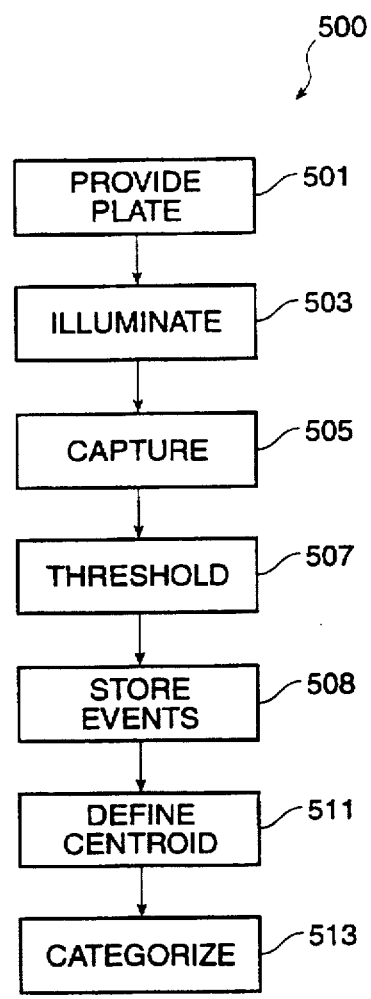
FIG. 5 is a simplified flow diagram of a method according to the present invention.

Details of this method are provided in reference to FIG. 5. This method, however, is merely an example of the present invention, and should not be construed as limited the claims as defined herein. One of ordinary skill in the art would recognize other techniques for carrying out these present claims.

The method 500 generally comprises providing (step 501) a plate onto the plate holder. This plate is firmly placed onto the holder. A clamp attaches this plate to the stage to prevent its movement. This firmly placed plate tends to ensure accurate intensity measurements during subsequent measurement steps.

The method then provides a step 503 of illuminating the plate. This plate is illuminated using the present lighting techniques. Preferably, external lighting incident to the front-side of the plate and internal lighting provided through the plate side can be used. This step highlights external and internal optical anomalies. These optical anomalies include scratches, chips, particles, gouges, voids, and the like.

The plate image is captured (step 505) by CCD cameras. If the CCD array does not cover the plate, an x-y stage can be used. If sufficient cameras are employed, however, the x-y stage is not necessary. These CCD cameras capture images of the anomalies. The images are transferred to an image processor, which converts the images for storage in computer memory. Conventional image processing techniques can be used to capture and store these images. Of course, the technique used with depend upon the application.

The images are then thresholded (step 507). An image processor coupled to a computer compares these thresholded images to selected standards to define events. These events can be defined anomalies which fall outside the inspection criteria, e.g., rejects, etc. Each event is stored (step 508) into computer memory along with its location in a coordinate system, e.g., x-y, r-θ, etc. This storage step effectively files each event with its location.

Standard image processing techniques are then used to define a centroid (step 511) for each event. An example of this image processing technique is peak detection and image erosion. But other techniques also can be used depending upon the application.

Events are then categorized in step 513. This step selectively places events having similar characteristics in groupings. For example, events having a selected dimension are placed in one category. Events located on the front-side surface are placed in another category. Other categorization schemes also may be used depending upon the application.

In another aspect of the present invention, a technique for identifying the location of a defect or an anomaly in the plate is provided. This location can be a front-side surface location, a bulk medium location, and a back-side surface location. In one embodiment, this present method may be briefly outlined as follows.

(1) Provide plate onto the plate holder. (if CCD array does not cover the plate use an x-y stage)

(2) Adjust the z-location of the plate to a first out-of-focus location.

(3) Externally illuminate front-side surface of the plate.

(4) Measure.

(5) Internally illuminate bulk medium of the plate.

(6) Measure.

(7) Adjust z-location of the plate to a second out-of-focus location.

(8) Externally illuminate front-side surface of the plate.

(9) Measure.

(10) Internally illuminate bulk medium of the plate.

(11) Measure.

(12) Compare images from first out-of-focus location with images from second out-of-focus location.

(13) Identify location of anomalies based upon the comparing step.

(14) Categorize the anomalies based upon their location, e.g., top or bottom.

(15) Selectively apply a filter to the anomalies based upon their location.

(16) Step to other x-y areas if necessary.

Figure 6:
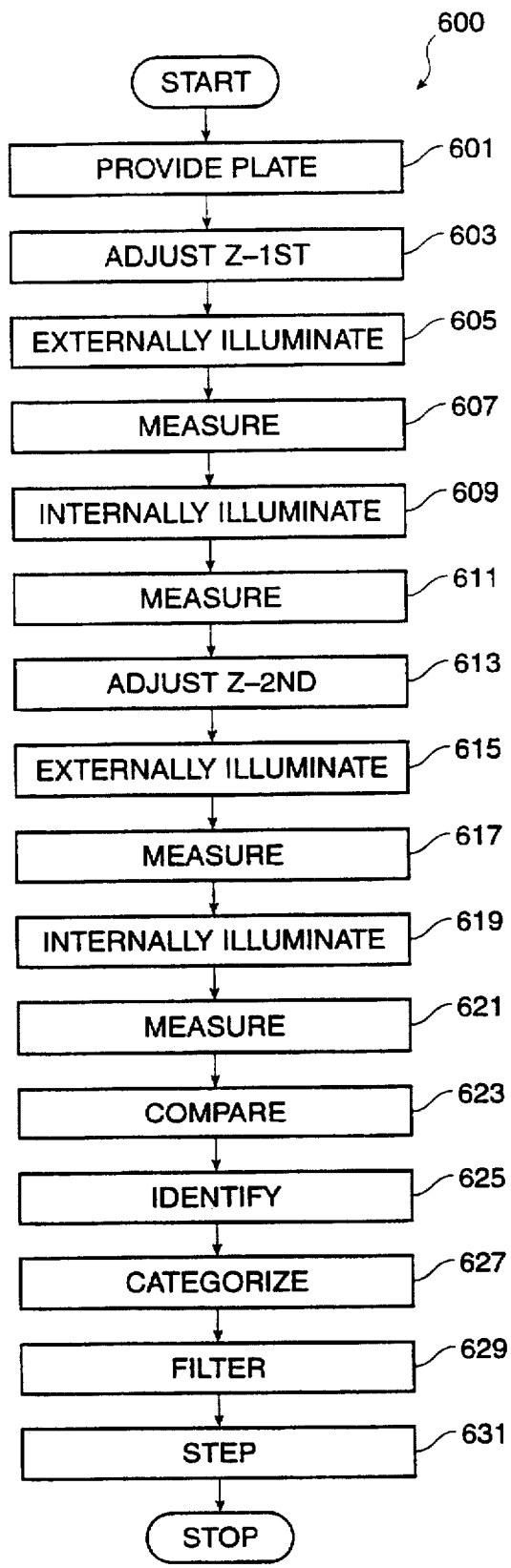
FIG. 6 is a simplified flow diagram of an alternative embodiment of a method according to the present invention.

Details of this method are provided in reference to FIG. 6. This method, however, is merely an example of the present invention, and should not be construed as limited the claims as defined herein. One of ordinary skill in the art would recognize other techniques, variations, or modifications for carrying out these present claims. In particular, the external illumination step (3) can be performed without the internal illumination step (5), or the internal illumination step (5) can be performed without the external illumination step (3). Alternatively, the method can perform steps (3) and (5) such that the bulk medium is illuminated using internal and external illumination steps (3) and (5) at the same time. In addition, the techniques described above are implemented using any one of the aforementioned embodiments and/or descriptions.

The method 600 generally comprises providing a plate (step 601) onto the plate holder or the x-y stage. This plate is firmly placed onto the stage. A clamp attaches this plate to the stage to prevent its movement. This firmly placed plate tends to ensure accurate intensity measurements during subsequent measurement steps.

The stage adjusts or lowers (step 603) the plate in the z-direction to a first out-of-focus location, which is generally a selected location where a selected portion of the plate is out-of-focus to the CCD cameras. The first out-of-focus location is generally a position directly above the front face of the plate. Alternatively, the CCD cameras are adjusted relative to the plate. Details with regard to the first out-of-focus location are shown with reference to the FIGS. below.

The method then provides a step of externally illuminating (step 605) the plate. This plate is illuminated using the present lighting techniques. External illumination (or lighting) incident to the front-side of the plate highlights external optical anomalies. These anomalies (i.e., surface anomalies) include scratches, chips, particles, gouges, voids, and the like, at or near the front-side plate face.

CCD cameras measure light intensity (step 607) from the plate at the first out-of-focus location to capture first images of surface anomalies at the first out-of-focus location. Characteristics for each anomaly are recorded, e.g., stored in memory. These characteristics include information such as x-y data, intensity measurements, signal proportional to focus position, and others.

The plate is then illuminated using an internal illumination (step 609) technique according to the present invention. In one embodiment, internal illumination is provided through the plate side. This step highlights internal optical anomalies. These optical anomalies include particles, gouges, voids, and the like, within the bulk plate volume. In some embodiments, internal and external illumination occur together. Alternatively, however, these types of illumination occur sequentially or at different times as described above.

CCD cameras measure light intensity (step 611) from the plate at the first out-of-focus location to capture images of internal anomalies at the first out-of-focus location. Characteristics for each internal anomaly are recorded, e.g., stored in memory. These characteristics include information such as x-y data, intensity measurements, signal proportional to focus position, and others.

Next, the stage adjusts or raises (step 613) the plate in the z-direction to a second out-of-focus location. External illumination (step 615) is then provided on the plate. CCD cameras measure light intensity (step 617) from the plate at the second out-of-focus location to capture second images of the surface anomalies at the second out-of-focus location. During this step, characteristics (e.g., x-location, y-location, intensity, etc.) of each anomaly also are recorded. Preferably, only the intensity of each of the anomalies change between the first out-of-focus location and the second out-of-focus location, since the x-location and the y-location should remain the same. Internal illumination (619) is provided via plate side. The CCD cameras measure light intensity (step 621) to capture second images of the internal anomalies at the second out-of-focus location.

The above method can be performed using a variety of illumination and measuring techniques as shown above and further explained herein. For instance, steps 605, 607, 609, and 611 can be performed serially. Alternatively, steps 605 and 607 can be performed without steps 609 and 611. Alternatively, steps 609 and 611 can be performed without steps 605 and 607. In still other embodiments, these variations can be further combined with steps 615, 617, 619, and 621. For instance, any of the above variations can be performed along with steps 615, 617, 619, and 621, which occur serially. Alternatively, steps 615 and 617 can be performed without steps 619 and 621. Alternatively, steps 619 and 621 can be performed without steps 615 and 617. Accordingly, external and internal illumination can occur together at a selected time. Alternatively, they can occur at different selected times as shown above or only one illumination method can be used to provide illumination to the plate without the other. These steps are often selected according to the particular application.

The method then compares (step 623) the characteristics of the images at the first out-of-focus location with the images at the second out-of-focus location to identify (step 625) the z-location of each of the anomalies. These characteristics include the intensity measurements. Each anomaly is categorized in step 627, and then the anomalies are selectively filtered (step 629) to highlight the selected anomalies. In some embodiments, the CCD cameras are stepped or moved (step 631) to other locations to capture images of anomalies at first and second out-of-focus locations. Details with regard to these techniques are described below.

Figure 7:
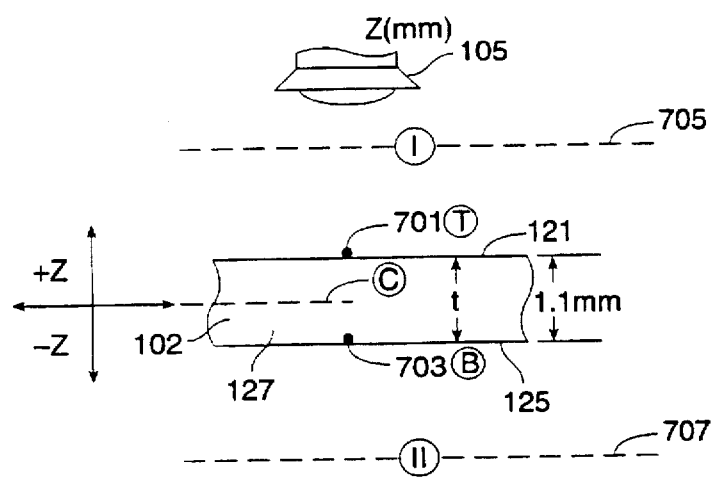
FIG. 7 is a side-view diagram of the plate and its out-of-focus locations according to the present invention.
Figure 8:
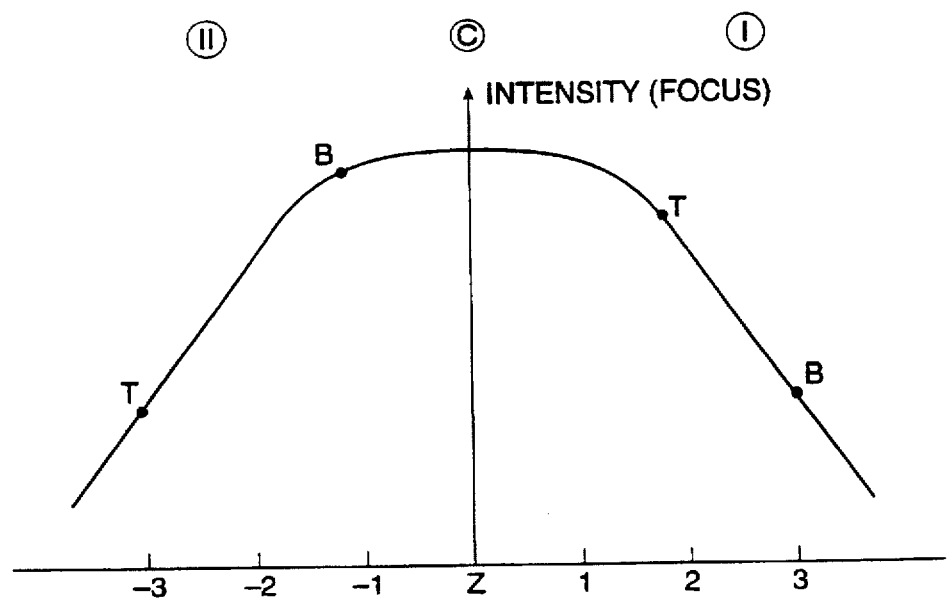
FIG. 8 is a plot of measured intensities of anomalies in the plate against the z-direction according to the present invention.

An example of this method can be illustrated by the simplified diagrams of FIGS. 7 and 8. FIG. 7 illustrates the plate 102 and its out-of-focus locations 705, 707. The plate is about 1.1 mm thick and is made of glass. As previously noted, CCD cameras 105 and lighting are applied to the plate. The plate 102 also includes an anomaly on the front-side surface 701 (or top surface) represented as "T" and an anomaly on the back-side surface 703 represented as "B."

A zero point on the z-axis is defined as a point in the center "C" of the plate thickness. CCD cameras are focused onto this zero point or object point as illustrated by the Figs. As shown, FIG. 8 is a simplified plot of intensity values plotted against z-axis displacement for anomalies at out-of-focus locations. Intensity or focus at this zero point does not substantially change with any displacement of the front-side surface in reference to the CCD cameras along the z-direction, as illustrated by FIG. 8. Near the zero point, the CCD cameras have a large depth of field.

The stage adjusts the plate to the first out-of-focus location. The first out-of-focus location 705 (e.g., 0.25 mm, 0.5 mm, 1.0 mm, etc. above plate) is defined by reference numeral "I" above the front-side surface. Intensity or focus decreases with respect to the displacement of the CCD camera along the positive z-direction (e.g., 1 mm to 3 mm, etc.), as illustrated by FIG. 8. This decrease in intensity with respect to anomaly location is monotonic. Depth of field for the CCD cameras is smaller than the top/bottom particle displacement. Therefore, the anomaly T on the front-side surface has a larger intensity value than the intensity of the anomaly B on the back-side surface. CCD cameras observe the plate with these anomalies, and capture first images of anomalies T and B at this first out-of-focus location.

The z-stage adjusts the plate to the second out-of-focus location. The second out-of-focus location 707 (e.g., 0.25 mm, 0.5 mm, 1.0 mm, etc. below plate) is defined by reference letter II. Intensity or focus decreases with increasing displacement values along the negative z-direction (e.g., −1 mm to −3 mm, etc.) when the CCD cameras are focused at this second out-of-focus location. The relationship is roughly linear. Depth of field is also smaller at the second out-of-focus location than the T/B displacement in the z-axis. Thus, a lower intensity value is registered or detected from the top anomaly T, and a higher intensity value is registered or detected from the bottom anomaly B. CCD cameras observe the plate for these anomalies, and capture second images of anomalies A and B.

The method then compares the first images with the second images. In particular, the first image of the top anomaly T at the first out-of-focus location is compared to the second image of the top anomaly T at the second out-of-focus location. Subtracting the intensity value of this first image with the intensity value of this second image yields a positive number. The positive number identifies an anomaly located on the top-side of the plate. The first image of the bottom anomaly B at the first out-of-focus location is compared to the second image of the bottom anomaly B at the second out-of-focus location. Intensity value of the first image of the bottom anomaly is subtracted from the intensity value of the second image of the bottom anomaly. This subtraction yields a negative number, identifying an anomaly located on the back-side surface. Accordingly, positive numbers designate anomalies located on the front-side surface and negative numbers designate anomalies located on the back-side surface.

Figure 9:
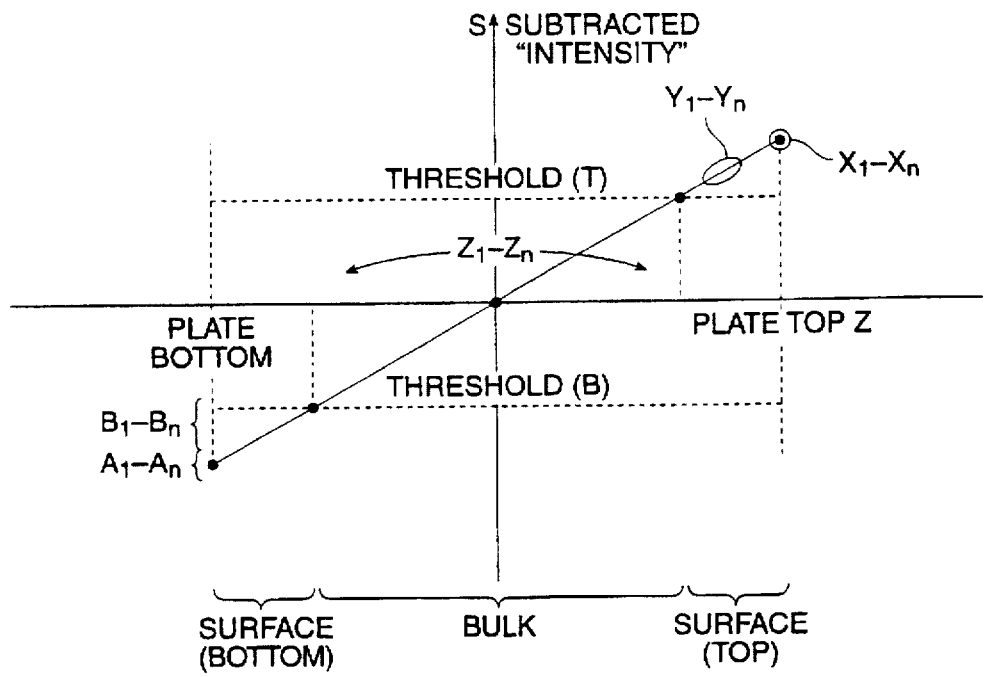
FIG. 9 is a simplified diagram of subtracted intensity against plate location.

In alternative embodiments, subtracting intensity values from an anomaly at a first out-of-focus location with the same anomaly at its second out-of-focus location yields difference values that can be placed in more detailed categorizes. FIG. 9 illustrates these subtracted intensity values (S) against z-locations (Z), e.g., top, bulk, bottom, etc. Difference values (i.e., intensities) ranging from "X1" to "XN" can represent anomalies on the front-side surface. Difference values ranging from "Y1" to "YN" can represent anomalies underlying on and contact with the front-side surface. Difference values ranging from "Z1" to "ZN" can represent anomalies in the bulk medium of the plate. Difference values ranging from "A1" to "AN" can represent anomalies underlying on and contact with the back-side surface. And, difference values ranging from "B1" to "BN" can represent anomalies on the backside surface.

Figure 10:
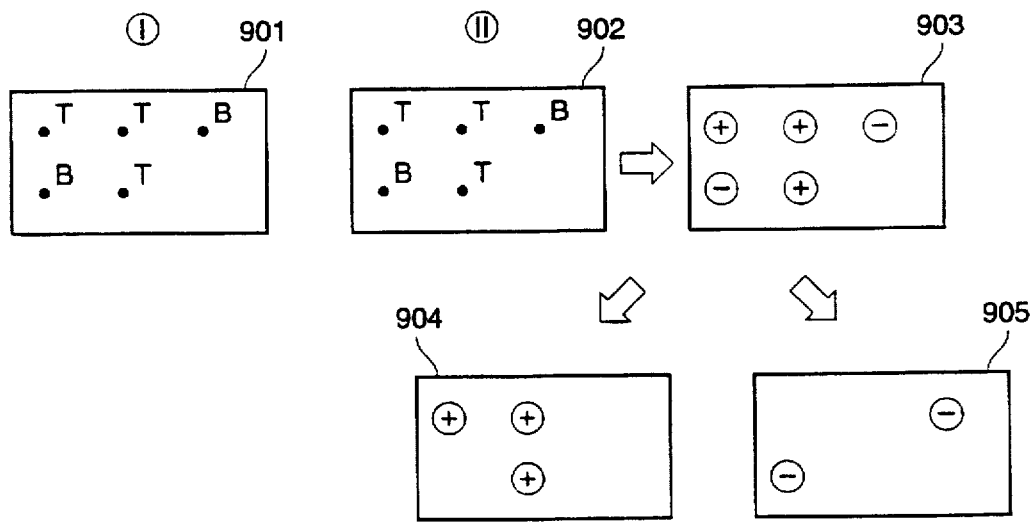
FIG. 10 is a series of diagrams depicting a filtering method according to the present invention.

A further example of the present technique is illustrated with reference to FIG. 10. At a first out-of-focus location 901, CCD cameras observe and capture intensity values along with respective x-y coordinate data for each of the anomalies "T" on the front-side surface and each of the anomalies "B" on the backside surface of the plate. The plate is adjusted to its second out-of-focus location 902. The CCD cameras observe the plate and capture intensity values along with respective x-y coordinate data for each of the anomalies T and B. An image processor compares intensities of each anomaly at the first out-of-focus location and the second out-of-focus location. This comparing step subtracts the intensity value of an anomaly at the first out-of-focus location with the intensity value of the same anomaly at the second out-of-focus location. Results of this process produce a plurality of numbers, e.g., positive and negative. These numbers 903 are shown by the "+" representing a positive number, and "−" representing a negative number. Filters can be used to separate the positive numbers 904 from the negative numbers 905. Positive numbers correspond to anomalies located on the front-side of the plate, and negative numbers correspond to anomalies located on the back-side of the plate. By separating the negative numbers from positive, the z-location of each of the anomalies is identified.

The invention has now been explained with reference to specific embodiments. Other embodiments will be apparent to those of ordinary skill in the art in light of the disclosure. It is therefore not intended that this invention be limited, except as indicated by the appended claims.

What is claimed is:

1. Method for locating defects on a first surface, on a second surface, and in a transparent planar medium with an optical image area defect monitoring tool, said method comprising the steps of:

illuminating said planar medium at an angle to an inspection axis, said inspection axis being substantially normal to said planar medium, in order to highlight external and internal optical anomalies;

capturing first images of said anomalies in a first vertical position away from a center of said planar medium at a first out-of-focus location on a first side of said planar medium and identifying said first images as first events in two-dimensional locations;

capturing second images of said anomalies in a second vertical position away from a center of said planar medium at a second out-of-focus location on a second side of said planar medium opposite to said first side and identifying said second images as second events in two-dimensional locations; and processing said first and second images to generate a corresponding first signal level and a second signal level, wherein differences between said first signal level and said second signal level are indicative of a z-location of said anomalies along said inspection axis.

2. The method of claim 1 wherein said processing step comprises subtracting said first signal level from said second signal level.

3. The method of claim 1 wherein said processing step comprises thresholding said first signal level relative to said second signal level, said thresholding step producing a result identifying said z-location of said anomalies.

4. The method of claim 3 wherein said processing step comprises thresholding said first signal level relative to said second signal level, said thresholding step establishing said z-location among a top surface, a bottom surface, and bulk.

5. The method of claim 1 wherein said illuminating step comprises illuminating capturing step said first surface from a source disposed at an acute angle to said first surface to effect light scattering from surface anomalies.

6. The method of claim 5 wherein said surface anomalies include surface chips, notches, surface voids, surface scratches, and surface particulates.

7. The method of claim 5 wherein said illuminating step further comprises illuminating by coupling light directly into an edge of said planar medium to effect light scattering from bulk anomalies while minimizing illumination of surface particles.

8. The method of claim 7 wherein said bulk anomalies include bulk voids, bulk cracks, and bulk particles.

9. The method of claim 1 wherein said capturing step is provided by an array of CCD cameras.

10. Apparatus for locating defects on a first surface, on a second surface, and in a transparent planar medium with an optical image area defect monitoring tool, said apparatus comprises:

a light source for illuminating said planar medium at an angle to an inspection axis, said inspection axis being substantially normal to said planar medium, in order to highlight external and internal optical anomalies; and a CCD camera operably coupled to an image processor, said CCD camera and image processor capturing first images of said anomalies in a first vertical position away from a center of said planar medium at a first out-of-focus location on a first side of said planar medium and identifying said first images as first events in two-dimensional locations, said CCD camera and said image processor capturing second images of said anomalies in a second vertical position away from a center of said planar medium at a second out-of-focus location on a second side of said planar medium opposite to said first side and identifying said second images as second events in two-dimensional locations;

wherein said image processor processing said first and second images to generate a corresponding first signal level and said second signal level, and differences between said first signal level and a second signal level are indicative of a z-location of said anomalies along said inspection axis.

11. Apparatus of claim 10 wherein said image processor subtracts said first signal level from said second signal level.

12. Apparatus of claim 10 wherein said image processor thresholds said first signal level relative to said second signal level to produce a result identifying said z-location of said anomalies.

13. Apparatus of claim 12 wherein said z-location is a top surface, a bottom surface, and bulk.

14. Apparatus of claim 10 wherein said light source comprises a first light source used to illuminated a first surface, said first light source being disposed at an acute angle to said first surface to effect light scattering from surface anomalies.

15. Apparatus of claim 14 wherein said surface anomalies include surface chips, notches, surface voids, surface scratches, and surface particulates.

16. Apparatus of claim 14 wherein said light source further comprises a second light source used to illuminate said planar medium by coupling light directly into an edge of said planar medium to effect light scattering from bulk anomalies while minimizing illumination of surface particles.

17. Apparatus of claim 16 wherein said bulk anomalies include bulk voids, bulk cracks, and bulk particles.

18. Apparatus of claim 10 wherein said CCD camera is an array of CCD cameras.

19. Apparatus of claim 10 wherein said CCD camera is an array of 64 CCD cameras.

20. Apparatus of claim 10 further comprising an x-y stage.

21. Method of fabricating a flat panel display, said method comprising:

illuminating a glass plate used for a flat panel display at an angle to an inspection axis, said inspection axis being substantially normal to glass plate, in order to highlight external and internal optical anomalies;

capturing first images of said anomalies in a first vertical position away from a center of said glass plate at a first out-of-focus location on a first side of said glass plate and identifying said first images as first events in two-dimensional locations;

capturing second images of said anomalies in a second vertical position away from a center of glass plate at a second out-of-focus location on a second side of said glass plate opposite to said first side and identifying said second images as second events in two-dimensional locations; and processing said first and second images to generate a corresponding first signal level and a second signal level, wherein differences between said first signal level and said second signal level are indicative of a z-location of said anomalies along said inspection axis.

22. The method of claim 21 wherein said first out-of-focus location is about 0.5 mm and greater above said glass plate.

23. The method of claim 21 wherein said second out-of-focus location is about 0.5 mm and greater below said glass plate.

* * * * *

UNITED STATES PATENT AND TRADEMARK OFFICE
CERTIFICATE OF CORRECTION

PATENT NO. : 5,790,247
DATED : August 4, 1998
INVENTOR(S) : Francois J. Henley et al.

It is certified that error appears in the above-identified patent and that said Letters Patent is hereby corrected as shown below:

<u>Title page,</u>
Item [62], Related U.S. Application Data , please add the following:
-- This application claims priority to Provisional Application 60/005,058 filed on October 6, 1995 which is hereby incorporated by reference for all purposes --

Signed and Sealed this

Eighth Day of February, 2005

JON W. DUDAS
*Director of the United States Patent and Trademark Office*